United States Patent [19]
Nygren et al.

[11] Patent Number: 6,105,174
[45] Date of Patent: Aug. 22, 2000

[54] MALE INCONTINENCE POUCH

[75] Inventors: Lars Nygren, Molndal; Dan Karlsten, Gothenburg; Lars Mattsson, Hallingsjo; Lars Stromberg, Molnlyoke, all of Sweden

[73] Assignee: Sorbinco Maskin AB, Sweden

[21] Appl. No.: 09/331,338

[22] PCT Filed: Dec. 19, 1997

[86] PCT No.: PCT/SE97/02186

§ 371 Date: Jun. 15, 1999

§ 102(e) Date: Jun. 15, 1999

[87] PCT Pub. No.: WO98/29061

PCT Pub. Date: Jul. 9, 1998

[30] Foreign Application Priority Data

Dec. 27, 1996 [SE] Sweden .................................. 9604840

[51] Int. Cl.$^7$ .................................. A41B 9/00; A61F 5/44
[52] U.S. Cl. .................................. 2/403; 2/400; 604/349; 604/385.1
[58] Field of Search .................... 2/400, 403; 604/385.1, 604/37, 394, 392, 393, 398, 358, 346–349, 304, 308, 317, 327, 355, 350–353; 602/67–73, 79, 58, 41

[56] References Cited

U.S. PATENT DOCUMENTS

| | | | |
|---|---|---|---|
| 2,933,085 | 4/1960 | Jacques | 602/67 |
| 3,570,491 | 3/1971 | Sneider . | |
| 4,182,334 | 1/1980 | Johnson | 602/67 |
| 4,197,849 | 4/1980 | Bosick | 602/67 |
| 4,200,103 | 4/1980 | Black et al. . | |
| 4,453,938 | 6/1984 | Brendling | 604/346 |
| 4,590,931 | 5/1986 | Kidwell, Jr. | 604/349 |
| 4,627,846 | 12/1986 | Ternstrom | 604/349 |
| 4,710,188 | 12/1987 | Runeman | 604/385.1 |
| 4,731,063 | 3/1988 | Newkirk | 604/347 |
| 5,716,350 | 2/1998 | Ryan | 604/385.1 |
| 5,935,091 | 8/1999 | Friedman | 602/79 |

FOREIGN PATENT DOCUMENTS

WO9107156  5/1991  European Pat. Off. .

*Primary Examiner*—Gloria M. Hale
*Attorney, Agent, or Firm*—Fasth Law Offices; Rolf Fasth

[57] ABSTRACT

The male incontinence pouch allows the user to determine for himself whether he wishes to apply the pouch around the penis only or the penis and scrotum. The incontinence pouch has an outer liquid-proof polyethylene layer. A soft fibrous nonwoven material is attached to the polyethylene layer. An inner liquid-permeable material is applied to the nonwoven material. An absorption layer is disposed between the polyethylene layer and the liquid-permeable material to form a laminate. An edge portion of the liquid-permeable material is attached to another edge portion of the liquid-permeable material so that a cavity is formed therebetween at a short side surface of the incontinence pouch. The laminate is folded inwardly along a main folding line so that a side wall is formed, the side wall has an inside and an outside so that the inside has an outer base line and the short side surface has an inner base line. An underside and an upperside are formed by conically folding the inside outwardly along a top folding line to form a pleat. The top folding line is disposed between the outer base line and the inner base line. The underside is delineated by the inner base line and the top folding line. The upperside is delineated by the outer base line and the top folding line. The pleat permits an increase in available length of the upper edge.-Remarks Reconsideration of the application is respectfully requested. The specification was rejected due to improper idiomatic English. The specification has now been rewritten and should be in full conformance.

7 Claims, 1 Drawing Sheet

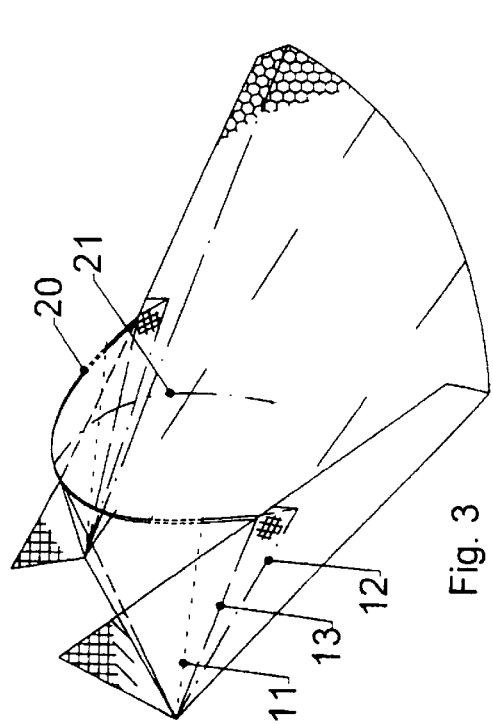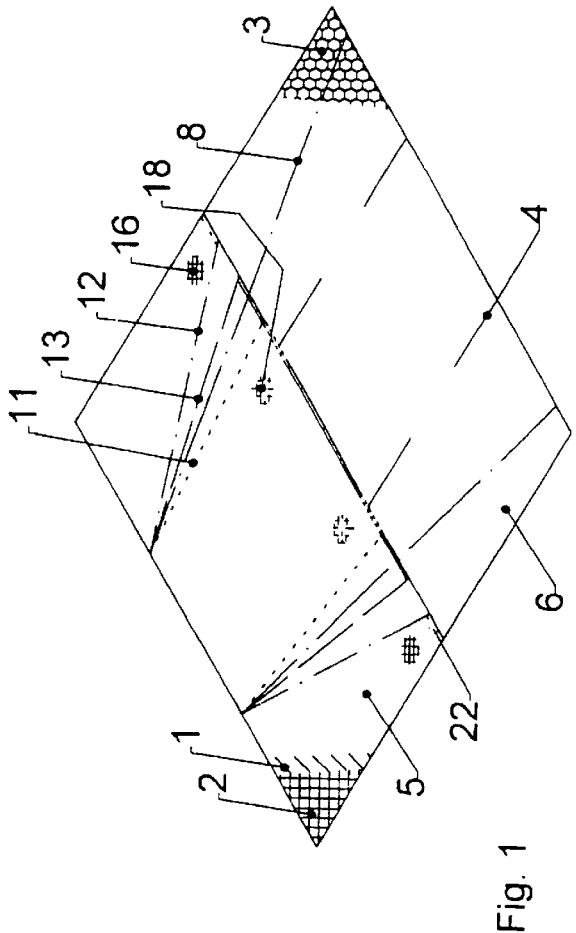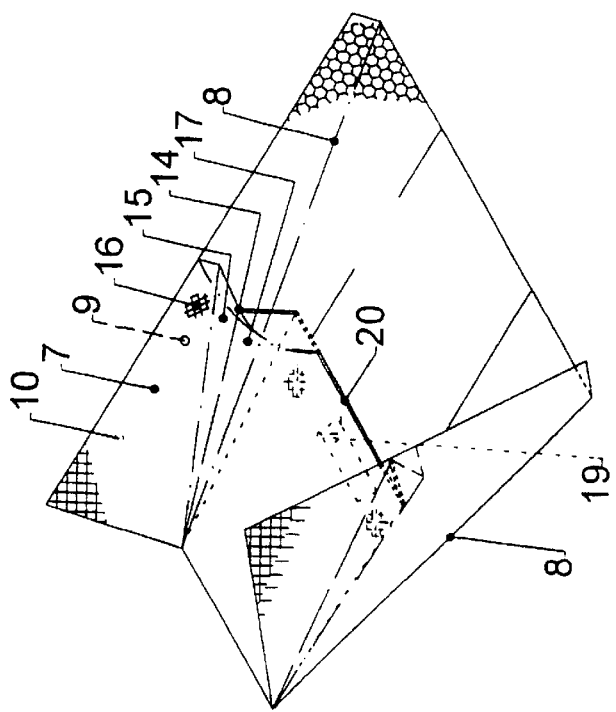

MALE INCONTINENCE POUCH

TECHNICAL FIELD

The present invention relates to a male incontinence pouch intended to give the user an optimally designed product where freedom of choice is conferred to determine for himself whether he desires an applicable pouch around the penis alone or the penis and scrotum, specifically insofar that the depth of the pouch, i.e., the Y-axis in a 3-dimensional view can thus be adapted. For example, the incontinence pouch in both application versions is equally wide in its 3-dimensional X-axis.

BACKGROUND AND SUMMARY OF THE INVENTION

The purpose of the present invention is the eliminate the known drawbacks that impair existing incontinence pouches. In an incontinence pouch known from patent SE-8303663-2 there is as patent criterion a recess around the scrotum in order to accommodate both penis and scrotum. In other words, one has optimized the incontinence pouch for men with what is termed a retracted penis. And in another incontinence pouch known from patent SE-8400056-1 it is stated with regard in its male version that the incontinence pouch is characterized by being used for the opposite purpose, namely solely for penile application. It is also so with the other incontinence pouches commercially available on the market. This is also confirmed by the fact that there is today no form of incontinence pouch that basically functions well for these two means of application.

This is achieved in accordance with the invention by means of a specific 2-stage pleat in its 3-dimensional X-axis, which upon application is optimally adapted when the Y-axis can thus be used in two stages, for the penis only or for penis and scrotum since a downwards hanging, somewhat flared, angled natural U-shape is formed, that is anatomically suitable for enclosing the scrotum.

This differs from SE-8303663-2 which version with its recess implies that men with what is termed a normal penis can more easily slide out of the recess in the incontinence pouch and that overfilling definitely occurs more easily with this relatively deeper recess, especially in what are termed sitting postures.

The SE-8400056-1 version excludes men with a retracted penis for scrotal application as it is too narrow, for which reason this incontinence pouch is now sold to for normal penile application solely. Should the pouch be used for men with a retracted penis, the penis will easily slide out, whereby the small available overlapping absorbent surface in the incontinence pouch will imply a guaranteed major risk of leakage. Under the existing patent criteria there is no means of generating a functioning pouch intend to enclose both penis and scrotum.

BRIEF DESCRIPTION OF THE DRAWINGS

FIG. 1 is a perspective view of the male incontinence pouch of the present invention in a flat position;

FIG. 2 is a perspective view of the male incontinence pouch of the present invention in a partially folded position; and FIG. 3 is a perspective view of the male incontinence pouch of the present invention in a fully operational position.

DETAILED DESCRIPTION

The incontinence pouch shown in FIGS. 1–3 comprises an outer liquid-proof layer (1), such as a polyethylene film layer that may be provided with a soft fibrous material (2), such as a nonwoven material, on its exterior surface. The material (2) may be used to avoid having the polyethylene film layer to be applied directly against the body. The incontinence pouch also has an inner liquid-permeable material (3). The pouch also has an absorption body (4) that is applied directly between the liquid-proof layer (1) and the liquid-permeable material (3) so as to form a bag shape by folding and sealing the material (3) against another portion of the material (3). The area where the material (3) is folded and sealed against the same material (3) forms a short side surface (5) intended to face the body and that is 40%–60% shorter than the long side surface (6) that is intended to be placed against underwear or the like.

A side portion (7) is delineated by a main folding line (8) and may be folded inwardly towards the short side surface (5). An outside (9) and an inside (10) of the side portion (7) are thus formed and both sides have an equal length. However, a pleat (14) may be obtained by double-folding the inside (10) outwardly along an inner base line (11) and outer base line (12) with a top fold line (13) located between them. The pleat (14) has an upper side (15) that is attached to the opposite inside (10) with a permanent adhesive (16). An underside (17) of the pleat (14) is removably attached to the short side surface (5) by an adhesive (18). An alternative to the adhesive (18) is a separatable ribbon (19) or the like that may be attached to the outsides (9) and extend across the sides (7). Adhesive in this context may refer to a variety of sealing material such as glue, cold-glue, hot-melt, lacquer, wax, VELCRO loop fasteners, zip ribbons, etc. It is to be understood that the removable adhesive (18) may not be applied at all so that the pouch is then primarily adapted for men with a retracted penis where the fold itself may be unfolded during application. The removable adhesive (18) may be replaced by a permanent adhesive (16) so that the pouch is primarily adapted for men with a normal penis.

When using the incontinence pouch for a normal penis, the incontinence pouch may be used without separating the removable adhesive (18) or the separatable ribbon (19). An upper edge (20) of the short side surface (5) may be raised to an optimal highest position when the removable adhesive (18) or the separable ribbon (19) has been separated. The angle of the outer base line (12) relative to the pleat (14) determines the length of the upper edge (20) and the pull-down angle (21). Also, the position of the outer base line (12) on the upper edge (20) in relation to where the side-edge seal is located, affects the length of the upper edge (20). That is, if the location of the outer base line (12) on the upper edge (20) is below the side-edge seal, the distance between them will produce an increase of the width of the available upper edge (20). It thus follows that if this distance is in any way sealed, this increase is eliminated. This alternative may be desirable if the permanent adhesive (16) has not been applied and it is possible to obtain a determination of the width of the upper edge (20) without having to fold the pleat (14) inwardly. This alternative is also desirable if the adhesive (16) is replaced with the removable adhesive (18) which also, in this case, produces a 2-step product also that is both adapted for normal penile and penile-scrotal applications. A relative drawback is that when the short-side surface (5) is not attached to the inside (10), an opening can be obtaining there during the application.

In practice, the present invention may, in one and the same product, be optimized for a penis only or the combination of a penis and scrotum. This is partly due to the upper edge (20) of the short side surface (5) that is like a cylindrical container and may be applied at the root of the penis when used for a penis only. When applied to the combination of a penis and scrotum, the upper edge (20) may be removed and pulled down and adapted in an anatomically correct manner so that the upper edge (20) is a downwardly hanging and somewhat outwardly angled U-shape.

What is claimed is:

1. A male incontinence pouch comprising:

an outer liquid-proof polyethylene layer having an exterior surface;

a soft fibrous nonwoven material applied to the exterior surface;

an inner liquid-permeable material applied to the nonwoven material;

an absorption layer disposed between the polyethylene layer and the liquid-permeable material to form a laminate;

an edge portion of the liquid-permeable material being attached to another edge portion of the liquid-permeable material so that a cavity is formed therebetween at a short side surface of the incontinence pouch;

the laminate being folded inwardly along a main folding line so that a side wall is formed, the side wall having an inside and an outside, the inside having an outer base line, the short side surface having an inner base line; and an underside and an upperside being formed by conically folding the inside outwardly along a top folding line to form a pleat, the top folding line being disposed between the outer base line and the inner base line, the underside being delineated by the inner base line and the top folding line, the upperside being delineated by the outer base line and the top folding line, the pleat permitting an increase of a length of an upper edge of the short side surface, the upper edge being movable between a closed position and an opened position, the pleat being foldable when the main folding line is congruent with the outer base line.

2. The male incontinence pouch according to claim 1 wherein the length of the upper edge is freely determinable in steps by applying a permanent non-removable adhesive attached to the upperside and a portion of the inside that is facing the upperside and by applying a removable adhesive attached to the underside and a portion of the short side surface that is facing the underside.

3. The male incontinence pouch according to claim 1 wherein the upperside is removably attached to the inside.

4. The male incontinence pouch according to claim 1 wherein the underside is attached to the short side surface with a separatable ribbon.

5. The male incontinence pouch according to claim 1 wherein a portion of the short side surface is attached to a portion of a long side surface of the male incontinence pouch.

6. The male incontinence pouch according to claim 1 wherein the main folding line intersects the outer base line.

7. The male incontinence pouch according to claim 1 wherein the underside is attached to the short side surface with a permanent non-removable adhesive.

* * * * *